US 6,399,596 B1

(12) United States Patent
Omilinsky

(10) Patent No.: US 6,399,596 B1
(45) Date of Patent: Jun. 4, 2002

(54) AVERMECTIN PESTICIDE WITH AN ORGANOSILICONE SURFACTANT

(75) Inventor: Barry Omilinsky, deceased, late of Princeton, NJ (US), by Marlene Omilinsky, executrix

(73) Assignee: Ocapco, Inc., Princeton, NJ (US)

( * ) Notice: Subject to any disclaimer, the term of this patent is extended or adjusted under 35 U.S.C. 154(b) by 0 days.

(21) Appl. No.: 09/902,803

(22) Filed: Jul. 12, 2001

Related U.S. Application Data
(60) Provisional application No. 60/217,736, filed on Jul. 12, 2000.

(51) Int. Cl.[7] ........................ A01N 43/00; A01N 25/00; A61K 31/33
(52) U.S. Cl. ....................................... 514/183; 424/405
(58) Field of Search ........................... 514/183; 424/405

(56) References Cited

U.S. PATENT DOCUMENTS

| | | |
|---|---|---|
| 4,560,677 A | 12/1985 | Dybas |
| 4,902,510 A | 2/1990 | Garden |
| 5,104,647 A | 4/1992 | Policello |
| 5,558,806 A | 9/1996 | Policello et al. |

FOREIGN PATENT DOCUMENTS

| | | |
|---|---|---|
| WO | WO 00/18825 A1 | 6/2000 |

OTHER PUBLICATIONS

Derwent on West, No. DE3602276, Knauf et al., "Synergistic Pesticidal Composition Containing Avermectin Derivatives", Aug. 6, 1987.

*Primary Examiner*—Alton Pryor
(74) *Attorney, Agent, or Firm*—Larson & Taylor PLC

(57) ABSTRACT

A pesticide composition is provided which is made from a pesticide compound, such as those from the avermectin family, and an organosilicone surfactant, such as polysiloxane, as the solvent for the pesticide. The use of the organosilicone surfactant as a solvent in conjunction with the avermectin pesticide in accordance with the present invention is advantageous in that it allows for control of pests such as nematodes and mites in substantially greater amounts for a longer period of time than has been accomplishing using prior art formulations including those which use similar concentrations of the active ingredient or those which use the pesticide in combination with an agricultural spray oil. In addition, a method is provided wherein pests can be reduced or eliminated from crops by application of an effective amount of the avermectin and organosilicone surfactant pesticide formulation of the present invention.

17 Claims, No Drawings

AVERMECTIN PESTICIDE WITH AN ORGANOSILICONE SURFACTANT

This application claims benefit of Provisional Application No. 60/217,736 filed Jul. 12, 2000.

FIELD OF THE INVENTION

This invention relates in general to the use of pesticides, such as those from the avermectin family, and an organosilicone surfactant as a solvent for the pesticide.

BACKGROUND OF THE INVENTION

Standard pesticide formulations such as those disclosed in U.S. Pat. Nos. 5,558,806 and 5,104,647, issued to Policello et al., incorporated herein by reference, utilize active ingredients such as abamectin solubilized in a formulation with a 1:1 ratio of an organosilicone surfactant such as polysiloxane with another ingredient such as Tergitol® "TMN-6" (trimethylnononal ethoxylate). However, when the active ingredient such as abamectin has been solubilized in the polysiloxane:TMN6 blend, the spreading of the material is detrimental to the efficacy of the pesticide.

Other pesticide formulations, such as those disclosed in U.S. Pat. No. 4,560,677 issued to Dybas, incorporated herein by reference, include an avermectin pesticide in combination with an agricultural spray oil which is added in the interest of extending the time period over which the pesticide will be effective. However, while some extension of the period of effectiveness is added by the use of the agricultural spray oil, the added time period is only achieved by virtue of the addition of the expensive spray oil, and thus the combination of avermectin with spray oils does not constitute an efficient or cost effective manner of achieving adequate coverage of pesticides for an extended period of time.

There is thus a distinct need in the field of pesticides to develop new formulations with solvents that result in a more efficient and efficacious pesticide, and which can be utilized in a more productive manner so as to reduce or eliminate the possibility of deleterious attack on plant crops by pests such as nematodes or mites. In addition, there is a distinct need in the field of pesticides to develop new formulations which can provide an effective and inexpensive pesticide for elongated periods of time without the need for the additional expense and complication of adding an agricultural spray oil.

SUMMARY OF THE INVENTION

Accordingly, it is thus an object of the present invention to provide a novel pesticide composition including an active ingredient such as those compounds of the avermectin family and an organosilicone surfactant as the solvent for the pesticide.

It is further an object of the present invention to provide a novel pesticide which utilizes an organosilicone surfactant as a solvent so as to provide superior mite control when compared to standard formulations at the same concentration of the active ingredient.

It is still further an object of the present invention to provide a novel pesticide composition which can be used to control mites in citrus and other crops, and which can also be utilized to control a wide variety of insects using a pesticide concentration that is less than those concentrations used in previous pesticide formulations.

It is even further an object of the present invention to provide a novel pesticide composition which can be used to provide extended and inexpensive crop treatment without the need for the expensive and complex addition of an agricultural spray oil.

These and other objects are achieved by virtue of the present invention which comprises a novel pesticide formulation comprising a pesticide, such as those of the avermectin family, and an organosilicone surfactant, such as polysiloxane, as the solvent for the pesticide. In addition, a method is provided wherein pests can be reduced or eliminated from crops by virtue of the use of the pesticide formulation of the present invention. The use of the organosilicone surfactant as a solvent in conjunction with the avermectin pesticide in accordance with the present invention has resulted in control of pests such as mites in substantially greater amounts for a longer period of time than has been accomplishing using prior art formulations including those which use similar concentrations of the active ingredient or those which use the pesticide in combination with an agricultural spray oil.

These and other features of the present invention as set forth in, or will become obvious from, the detailed description of the preferred embodiments provided hereinbelow.

DETAILED DESCRIPTION OF THE PREFERRED EMBODIMENTS

In accordance with the present invention, an improved pesticide is provided which involves the use of a variety of pesticides, such as those of the avermectin family, with an organosilicone surfactant, such as polysiloxane, as a solvent for the pesticide. In the preferred embodiment of the present invention, the pesticide that is used is one from the avermectin family of pesticides whose structures are closely related complex 16-membered lactones which exhibit synergistic effects when dissolved in the organosilicone material. These avermectin pesticides include compounds such as these have been disclosed in U.S. Pat. No. 4,560,677, incorporated herein by reference. The avermectin pesticide useful in the present invention thus may be any avermectin pesticide well known in the art, such as the avermectin compounds disclosed in U.S. Pat. No. 4,560,677 (issued to Dybas), or others well known in the art. One such particularly preferred pesticide is known as abamectin (or avermectin B-1) which can be utilized in accordance with the invention. Other avermectins useful in accordance with the invention are those classified as avermectin A1a, A1b, A2a, A2b, B1b, B1b, B2a, and B2b, having the formulas as described in U.S. Pat. No. 4,560,677.

However, although the present invention is known to be particularly useful with pesticides of the avermectin family, such as abamectin, the present invention will be useful with any pesticide that is compatible for use with an organosilicone surfactant. As will be recognized by one of ordinary skill in this art, a variety of pesticides may be employed in accordance with the present invention to accomplish crop protection against a variety of insect and other pests, and thus the particular pesticide to be used with the organosilicone surfactant of the invention will be dependent upon the type of crop involved and the particular pest for which is sought to be protected against. The present invention is designed to control a wide variety of pests that usually damage plants or crops, including nematodes, spider mites, other mites, and other common pests typically faced by plant species. The plants that can be protected using the present invention include numerous plants subject to pests including food crops and ornamental plants as well.

In the preferred embodiment, the pesticide composition in accordance with the present invention is prepared by placing an amount of the active ingredient, such as a pesticide of the avermectin family, in the range of approximately 0.001 to 25% by weight, the solubility limit of the active ingredient, with a preferred range of about 1–5%, into an organosilicone surfactant such as polysiloxane which will comprise approximately 75 to 99.999% by weight of the composition. As recited above, it is intended to indicate that these preferred weight percent amounts in the composition are those amounts which will be present in the resulting composition prior to any dilution. In this preferred embodiment, the avermectin family compound and the organosilicone surfactant are mixed in these weight percentages, and the resulting composition or concentrate may be utilized in this form, as would be the case for use by individuals in plants or gardens found in or around the home. However, when used in more industrial applications, such as for fields or crops, or for use with plants or foliage in a larger scale, this concentrated form of the composition of the invention may be diluted as necessary with an aqueous fluid, e.g., water, to any desired amount. Depending on the size of the actual application, ranging from relatively small areas to large fields of crops or other plants, the diluent, such as water, may be added in amounts ranging from a few liters to hundreds or thousands of gallons of aqueous liquid.

In any event, the avermectin:organosilicone ratio in the final preferred composition will thus range from about 0.001:100 (1:100,000) to about 25:75 (1:3) by weight. In the particularly preferred embodiment, the avermectin:organosilicone ratio will range from about 1:100 to about 5:75 (1:15) by weight.

In a particularly preferred embodiment utilizing an avermectin compound as an active ingredient, approximately 1–5 grams of avermectin is mixed into about 90–110 grams of polysiloxane. If the active material is less than 100% in purity, it is preferred that the material be corrected and the polysiloxane level be concomitantly reduced. In the preferred process of preparing the pesticide composition of the invention, this mixture is blended until the avermectin is dissolved in the polysiloxane. The polysiloxane preferably may also be warmed (e.g., to about 40° C. or other suitable temperature depending on the precise ingredients used) in order to facilitate and expedite the dissolution process. Finally, as set forth above, the formulation may be diluted with an appropriate amount of a suitable aqueous liquid such as water.

One particularly preferred polysiloxane which may be used in the invention is the polysiloxane known as trisiloxane-8-ethoxylate, but any polysiloxane that may be useable on plants and crops is suitable for use in the present invention. One preferred polysiloxane formulation utilized as the organosilicone surfactant of the invention is known as Silwet-77, and this formulation includes polyalkyleneoxide-modified heptamethyltrisiloxane at a level of about 84%, and allyloxypolyethyleneglycol methyl ether at a level of 16%. In preparing the composition of the present invention, as indicated above, an amount of the avermectin compound in the range of about 0.001% to about 25% by weight of the composition, and preferably about 1 to 5% of the overall composition, should be utilized to prepare the desired pesticide formulation. However, as set forth above, with regard to the use of the active avermectin ingredient, e.g., abamectin, if this active ingredient is utilized in a percentage of less than 100%, the material is preferably corrected and the polysiloxane is concomitantly reduced.

Once prepared in the manner stated above, or in any other conventional manner that would be employed to prepare a pesticide composition from ingredients as recited above, the avermectin pesticide compositions may be applied to crops in any suitable manner based on the size and nature of the plants or crops to be treated. The application of the pesticides of the present invention may be conducted in any of a number of suitable ways well known in this field. Such application procedures include spraying, pouring, hosing, or other conventional methods for applying a pesticide utilizing conventional equipment such as a spray hose, hand mister, crop duster, etc. In the preferred method, individual plants or crops are sprayed until dripping with the pesticide formulation of the present invention, and this can be done as many times as necessary for the particular plant or crop, e.g., daily, weekly, etc. depending on the plant or crop and the likelihood of pest infestation.

It is thus contemplated that the amount applied to the plants or crops will be that amount effective to reduce or eliminate damage to the plant or crop by pests such as mites. This effective amount will differ depending on the specific plant or crop being treated, as well as with the varying environmental conditions, e.g., temperature, water level, moisture levels, etc., that such plants or crops will be subject to. In addition, in circumstances where pest infestation is more likely, applications of the present pesticide may be increased as needed.

As utilized in the manner set forth above, the pesticide formulation of the present invention can thus be utilized advantageously to control a wide variety of insects using a pesticide concentration that is less than those concentrations used in previous pesticide formulations.

It is thus submitted that the foregoing embodiments are only illustrative of the claimed invention, and alternative embodiments well known or obvious to one skilled in the art not specifically set forth above also fall within the scope of the claims.

In addition, the following examples are presented as illustrative of the claimed invention, and are not deemed to be limiting of the scope of the invention, as defined by the claims appended hereto, in any manner.

EXAMPLES

Example 1

A composition is prepare by weighing an equivalent of approximately 2 grams of the active ingredient avermectin into about 98 grams of a polysiloxane. The polysiloxane material is described in the literature as trisiloxane-8-ethoxylkate. The material data sheet (trade name Silwet L-77) describes CAS#27306-78-1, polyalkyleneoxide modified heptamethyltrisiloxane at a level of 84%. Another component believed to be a by-product of the ethoxylation reaction is described as CAS#272-80-8, allyloxypolyethyleneglycol methyl ether at a level of 16%. The molecular formula is $(C_2H_4O)_n$ $C_{11}H_{30}O_3Si_3$. Where n=8, the molecular weight is 646. Accordingly, a range of 2 to 20 moles of ethylene oxide (or $C_2H_4O$) will provide a molecular range of 382 to 1174. With regard to the use of the active ingredient, e.g., avermectin, if the active material is utilized in a percentage of less than 100%, the material is preferably corrected and the polysiloxane is concomitantly reduced. In any event, the polysiloxane is preferably warmed to approximately 40° C. to speed dissolution. The composition in accordance with the present invention was thus applied in tests assessing the effectiveness of the pesticide in protection against pests such as nematodes and spider mites and was thus shown to be more effective against such pests than prior art formulations.

Example 3

The tests as described in Example 1 were expanded upon, and the following results with regard to testing of the compositions of the present invention were obtained as follows:

Overview

An assessment was made with regard to residual activity of Avermectin formulations against Two-spotted spider mites (TSSM) on ornamental plants.

Methods

Plants—Vinca (Vinca major) for this test was grown in a greenhouse environment to a height of ca 7 inches. Plants were fertilized (Peters 20-20-20, 1 teaspoon/gallon) once a week to promote healthy plant growth.

Treatments and Assessments—Plants were sprayed to drip using a hand mister and allowed to dry overnight (See treatment list below). Leaf discs, 20 mm in diameter, were cut from the vinca plants and placed on moistened cotton in small dishes. Five adult, female two-spotted spider mites (TSSM) were added to each leaf disc. These were four replicates for each treatment. Leaf discs were assessed at 48 hours to determine percent mortality and number of eggs per disc. Plants were returned to the greenhouse where they Example 2

Tests were conducted to compare the effectiveness of the present invention, a pesticide formulation in accordance with the invention designated as "OTX 951" which uses polysiloxane alone as the solvent was compared with the formulation disclosed in U.S. Pat. No. 5,558,806 which consists of a blend of polysiloxane and the "TMN6" additive (Tergitol® as described above) in a 1:1 blend. The data accumulated with regard to the effectiveness of both of these formulations is summarized below in Table 1:

TABLE 1

| | % Mortality Two Spotted Spider Mite 2 oz/100 gallons | | | |
|---|---|---|---|---|
| Treatment | Initial | 7 Days | 14 Days | 21 Days |
| Water | 10 | 5 | 0 | 0 |
| Agri-Mek | 100 | 85 | 35 | 45 |
| OTX 951 | 100 | 80 | 95 | 65 |
| OTX 956 | 100 | 80 | 50 | 35 |
| OTX 957 | 100 | 80 | 45 | 45 |

As shown in Table 1 above, these data clearly show that when the abamectin is solubilized in the polysiloxane:TMN6 blend, the spreading of the material is detrimental to the efficacy of the pesticide as reflected in the superior results achieved by the polysiloxane formulation of the present invention. Utilizing the polysiloxane alone in accordance with the present invention is clearly more efficacious, and the experimental results achieved as reflected in Table 1 above show and improvement (in terms of mortality of spider mites) by greater than twice that achieved by the prior art formulation after 14 days. were bottomed watered for the remainder of the test period. Samples were taken from the plants at 0, 7, 14, 21, 28 and 35 days after treatment (DAT).

Statistical Results—All data were analyzed via ANOVA (SAS program) and means test was LSD (0.05% level). LSD analysis data are reported as transformed means.

Treatment List and Rates:
1. Water
2. Agri-Mek 0.15 lb EC 2 oz./100 gal.
3. OTX 951 18 g/L 2 oz./100 gal.
4. OTX 956 18 g/L 2 oz./100 gal.
5. OTX 957 18 g/L 2 oz./100 gal.

Experimental Results—Table 2 below shows a summary of the mortality and egg laying assessments of TSSM on vinca over a 35-day period, including some of the results included and discussed in Example 1, above. Means separation test analysis is shown in Table 3. Equal TSSM mortality counts were recorded on Agri-Mek and OTX 951 plants at 0 and 7 DAT. However, at 14 DAT and beyond, OTX 951 plants resulted in significantly improved control of TSSM. This trend continued until the end of the test (35 DAT). OTX 956 showed some improved activity over Agri-Mek up to 21 DAT and OTS 957 was ca equal to Agri-Mek throughout the test.

These tests thus support the conclusion that the OTX-951 formulation of the present invention offers a significant TSSM efficacy advantage over that of the Agri-Mek standard.

Example 4

Additional tests were conducted which assessed the pesticide composition of the present invention (referred to in the Tables below as OTX 951) on citrus fruits (e.g., oranges) as compared with formulations such as those described in U.S. Pat. No. 4,560,677 which include an agricultural spray oil in addition to the pesticide. As reflected in Tables 4–7 below, the tests showed that the use of the OTX-951 formulation of the present invention could be used effectively and for longer times than similar formulations which were used in conjunction with an expensive agricultural spray oil. Moreover, the pesticide compositions of the present invention were shown to be effective when used in lesser amounts than the standard treatment formulations.

Accordingly, the additional tests confirmed the improved efficacy of the OTX-951 formulation of the present invention over prior art formulations, such as those that required the use of an agricultural spray oil, as evidenced in the results shown in Tables 4–7. Once again, these tests evidenced the efficacy and significant advantages of the improvements provided by the present invention in terms of efficient and inexpensive use of agricultural pesticides for prolonged periods of time which are superior over prior art methods.

TABLE 2

| Trt | Mites Added 48 hours # Alive | % Mort | 48 hours # Eggs/Disc. |
|---|---|---|---|
| Time: 28 days | | | |
| Water | 5.0 | 0.0 | 29.0 |
| Agri-Mek 2 oz/100 gal | 2.5 | 50.0 | 5.5 |
| OTX 951 2 oz/100 gal | 1.5 | 70.0 | 8.8 |
| OTX 956 2 oz/100 gal | 3.5 | 30.0 | 20.0 |
| OTX 957 2 oz/100 gal | 2.5 | 50.0 | 11.0 |
| Time: 35 days | | | |
| Water | 5.0 | 0.0 | 46.0 |
| Agri-Mek 2 oz/100 gal | 3.0 | 40.0 | 14.8 |
| OTX 951 2 oz/100 gal | 2.0 | 60.0 | 14.5 |
| OTX 956 2 oz/100 gal | 3.3 | 35.0 | 13.8 |
| OTX 957 2 oz/100 gal | 3.0 | 40.0 | 16.0 |

TABLE 3

Statistical Analysis of TSSM Mortality Data

| t | Grouping | Mean | N | trt |
|---|---|---|---|---|
| LSD - Mortality Time 0 | | | | |
| | A | 1.57080 | 4 | 5 |
| | A | 1.57080 | 4 | 2 |
| | A | 1.57080 | 4 | 3 |
| | A | 1.57080 | 4 | 4 |
| | B | 0.24826 | 4 | 1 |
| LSD - Mortality Time 7 days | | | | |
| | A | 1.2843 | 4 | 2 |
| | A | 1.2339 | 4 | 3 |
| | A | 1.1687 | 4 | 5 |
| | A | 1.1687 | 4 | 4 |
| | B | 0.1399 | 4 | 1 |
| LSD - Mortality Time 14 days | | | | |
| | A | 1.4552 | 4 | 3 |
| | B | 0.7865 | 4 | 4 |
| | B | 0.7312 | 4 | 5 |
| | B | 0.5147 | 4 | 2 |
| | C | 0.0316 | 4 | 1 |
| LSD - Mortality Time 21 days | | | | |
| | A | 1.0077 | 4 | 3 |
| B | A | 0.7362 | 4 | 2 |
| B | A | 0.7312 | 4 | 5 |
| B | | 0.6257 | 4 | 4 |
| | C | 0.0316 | 4 | 1 |
| LSD - Mortality Time 28 days | | | | |
| | A | 1.0630 | 4 | 3 |
| B | A | 0.7914 | 4 | 2 |
| B | A | 0.7914 | 4 | 5 |
| B | C | 0.4594 | 4 | 4 |
| | C | 0.0316 | 4 | 1 |
| LSD - Mortality Time 35 days | | | | |
| | A | 0.8995 | 4 | 3 |
| B | A | 0.6279 | 4 | 5 |
| B | A | 0.6229 | 4 | 2 |
| B | A | 0.5726 | 4 | 4 |
| | B | 0.0316 | 4 | 1 |

TABLE 4

No. Mites/Lensfield/fruit

| Treatment | Rate (lbs ai/A) | Pre | 7 DAT | 21 DAT | 35 DAT | 49 DAT | 77 DAT |
|---|---|---|---|---|---|---|---|
| OTX 951 | 0.00625 | 0.72 | 0.66 | 0.26 | 0.03 | 0.16 | 0.95 |
| Agrimek | 0.00625 | 0.72 | 0.97 | 0.78 | 2.36 | 8.28 | 6.3 |
| Agrimek + Oil | 0.00625 + 7.5 gal | 2.6 | 0.36 | 0.75 | 2.08 | 6.33 | 6.3 |
| Micromite + Oil | 0.3 + 7.5 gal | 0.55 | 0.52 | 0.61 | 0.45 | 0.65 | 0.77 |
| Check | | 0.46 | 1.08 | 0.98 | 2.24 | 7.85 | 26.6 |

TABLE 5

No. Mites/Lensfield/fruit

| Treatment | Rate/A | Pre | 7 DAT | 28 DAT | 56 DAT | 70 DAT |
|---|---|---|---|---|---|---|
| OTX 951 | 5.0 oz | 4.6 | 0 | 0 | 0.01 | 0 |
| Alert + Oil | 9.5 oz | 6.00 | 0.00 | 0.00 | 0.00 | 0.00 |
| Agrimek + Oil | 10 oz + 8 gal | 5.5 | 0 | 0.06 | 0 | 0 |
| Micromite + Oil | 1.25 lbs + 8 gal | 5.8 | 0.02 | 0.07 | 0 | 0 |
| Check | | 4.9 | 260 | 3.4 | 1.93 | 0.23 |

TABLE 6

No. Mites/Lensfield/fruit

| Treatment | Rate (lbs ai/A) | Pre # | 21 DAT | 35 DAT | 56 DAT | 70 DAT | 84 DAT |
|---|---|---|---|---|---|---|---|
| OTX 951 | 5 oz | 2.01 | 0.04 | 0.05 | 0.09 | 0.18 | 0.24 |
| OTX 952 | 5 oz | 1.41 | 0.24 | 0.04 | 2.9 | 3.65 | 0.21 |
| Agrimek + Oil | 10 oz + 8 gal | 1.94 | 0 | 0.08 | 0.96 | 0.88 | 0.18 |
| Nexter 75 W + Oil | 6.6 oz + 8 gal | 1.45 | 0.07 | 0.92 | 4.4 | 4.23 | 2.03 |
| Check | | 1.88 | 0.81 | 1.65 | 3.96 | 4.98 | 1.04 |

TABLE 7

No. Mites-Lensfield/fruit

| Treatment | Rate (lbs ai/A) | Pre # | 7 DAT | 14 DAT | 28 DAT | 42 DAT | 56 DAT | 77 DAT |
|---|---|---|---|---|---|---|---|---|
| OTX 951 | 5 oz | 9.1 | 0.00 | 0.00 | 0.00 | 0.01 | 0.00 | 0.02 |
| Agrimek + Oil | 10 oz + 8 gal | 15.83 | 0.00 | 0.00 | 0.00 | 0.00 | 0.00 | 0.00 |
| Polyram 80 DF | 5 lbs. | 10.93 | 0.00 | 0.00 | 0.00 | 0.02 | 0.03 | 0.00 |
| Check | | 14.88 | 6.77 | 4.98 | 1.11 | 3.66 | 3.88 | 14.88 |

What is claimed is:

1. A composition for use as a pesticide, said composition consisting essentially of comprising an avermectin compound in the range of about 0.001 to 25% by weight and an organosilicone surfactant in the range of about 75 to 99.999% by weight.

2. The composition according to claim 1, wherein the avermectin compound is about 1–5% by weight.

3. The composition according to claim 1, wherein the organosilicone composition is about 95–99% by weight.

4. The composition according to claim 1, wherein the avermectin compound is an avermectin selected from the group consisting of avermectin A1a, A1b, A2a, A2b, B1a, B1b, B2a, and B2b.

5. The composition according to claim 1, wherein the avermectin compound is abamectin.

6. The composition according to claim 1, wherein the organosilicone compound is a polysiloxane.

7. The composition according to claim 6, wherein said polysiloxane is trisiloxane-8-ethoxylate.

8. The composition, according to claim 6, wherein the concentration of said polysiloxane is approximately 90–110 grams.

9. The composition according to claim 1, wherein the composition is diluted with a suitable amount of an aqueous diluent.

10. The composition according to claim 1, wherein the composition is diluted with water.

11. The composition, according to claim 1, wherein the concentration of said avermectin is approximately 1–5 grams.

12. A composition for use as a pesticide, said composition consisting essentially of an avermectin compound and a trisiloxane-8-ethoxylate, wherein said avermectin is in the range of approximately 1–5% by weight and said trisiloxane-8-ethoxylate is in the range of approximately 95–99% by weight.

13. The composition, according to claim 12, wherein the avermectin is in the range of about 1–5 grams and said trisiloxane-8-ethoxylate is present in an amount in the range of about 90–1 10 grams.

14. A composition for use as a pesticide, said composition consisting essentially of an avermectin compound and an organosilicone surfactant wherein the ratio of the avermectin compound to the organosilicone compound ranges from about 1:100,000 to about 1:3 by weight.

15. A composition according to claim 14 wherein the ratio of the avermectin compound to the organosilicone compound ranges from about 1:100 to about 1:15 by weight.

16. A method of treating plants or crops so as to prevent or reduce infestation by pests comprising applying an effective amount of the composition of claim 1 to said plants or crops.

17. A method of treating plants or crops so as to prevent or reduce infestation by pests comprising applying an effective amount of the composition of claim 14 to said plants or crops.

* * * * *